(12) United States Patent
Houston et al.

(10) Patent No.: US 6,416,144 B1
(45) Date of Patent: Jul. 9, 2002

(54) STERILIZER HORIZONTAL MOTORIZED SLIDING DOOR CLOSURE

(75) Inventors: John C. Houston; Mark E. Chiffon; Arthur T. Nagare; Aaron L. Hill, all of Erie, PA (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 09/540,662

(22) Filed: Mar. 31, 2000

(51) Int. Cl.[7] .......................... A47B 81/00; E05D 15/10
(52) U.S. Cl. .......................................... 312/209; 49/409
(58) Field of Search ................................ 312/209, 295, 312/296, 322, 319.1, 319.5; 49/409, 410, 360

(56) References Cited

U.S. PATENT DOCUMENTS

| | | | |
|---|---|---|---|
| 1,920,855 A | * 8/1933 | Gloekler | 312/295 |
| 4,651,469 A | * 3/1987 | Ngian et al. | 49/409 X |
| 5,076,018 A | * 12/1991 | Gianfranco | 49/410 |
| 5,195,790 A | 3/1993 | Bulko et al. | 292/201 |
| 5,237,777 A | 8/1993 | Houston et al. | |
| 5,239,781 A | 8/1993 | Napierkowski et al. | |
| 5,249,392 A | 10/1993 | Houston et al. | |
| 5,461,829 A | * 10/1995 | Lehto et al. | 49/419 |
| 6,017,105 A | 1/2000 | Goughnour et al. | 312/209 |

FOREIGN PATENT DOCUMENTS

| | | |
|---|---|---|
| CH | 604 728 | 9/1978 |
| WO | WO 83/01740 | 5/1983 |

* cited by examiner

*Primary Examiner*—James O. Hansen
(74) *Attorney, Agent, or Firm*—Fay, Sharpe, Fagan, Minnich & McKee, LLP

(57) ABSTRACT

A guidance assembly (28) guides a door (22) to a cabinet (10) while it is moved between an open position, in which access to an interior chamber is provided through an opening (16) in the cabinet, and a closed position, in which the door covers the opening. The guidance assembly includes two pivotable support members (90, 92) which are pivotally connected to the door. The pivotable support members each include a roller (110, 112) which rolls along a horizontal rail (80) mounted to an exterior wall (18) of the cabinet, adjacent an upper end of the opening. A door positioning system (130), comprising upper and lower door positioners (132, 134, 136), maintains a space between the door the cabinet during opening and closing the door. This prevents damage to the door and the exterior wall of the cabinet and to a sealing member (70) disposed between the door and the cabinet. As the door moves inward or outward, the pivotable support members pivot relative to the front face (46) of the door and U-shaped portions (142, 160) the door positioners flex to relieve any stresses placed on the rollers.

22 Claims, 9 Drawing Sheets

STERILIZER HORIZONTAL MOTORIZED SLIDING DOOR CLOSURE

BACKGROUND OF THE INVENTION

The present invention relates to the door closure arts. It finds particular application in conjunction with a horizontal sliding door for sealing the opening to a sterilization chamber and will be described with particular reference thereto. It should be appreciated, however, that the invention is also applicable to a wide variety of other closure systems.

In many applications, it is desirable to have a chamber door sealingly engage a chamber opening. A gasket, positioned between the door and the outside of the chamber, creates an airtight seal between the door and chamber opening. For large chambers, such as steam sterilizers, horizontal sliding doors are sometimes used to allow the door to be moved from the open to the closed position. During translation, the door is guided to preclude scraping of the front of the chamber and avoid damage to the seal. When closed, the door is provided with some freedom of axial movement so that the door is able to move in and out a small amount as the pressure changes inside the sterilizer. Without this slack, the movement of the door would place stresses on the guidance system, leading to premature failure.

To provide this axial movement, the guidance system commonly includes a combination of rollers and recessed tracks. Unique bracketing is often needed to mount the rollers and unique tracks are generally provided which have the sole purpose of guidance. Additionally, because of the recesses, the guidance system does not provide guidance, and thus seal protection, for the entire door translation.

U.S. pat. No. 6,017,105 to Goughnour, et al. provides a sliding door guidance method for a walk-in sterilizer in which recesses in guidance tracks above and below the door receive guidance rollers at the top and bottom of the door when the door is in the closed position. The rollers must properly engage the recesses, otherwise pressure on the rollers when the door translates could cause damage to the rollers and associated hardware.

To ensure that the door of a sterilizer remains locked during a sterilization cycle, many sterilizers employ an electronic or pneumatically controlled locking mechanism which uses a program or pressure switch to determine when the lock needs to be applied. Such devices add to the complexity of the sterilizer.

The present invention provides for a new and improved guidance method for a horizontal sliding door which overcomes the above-referenced problems and others.

SUMMARY OF THE INVENTION

In accordance with one aspect of the present invention, a sterilization or disinfection apparatus is provided. The apparatus includes a housing which defines an interior chamber and an opening. A door has an interior face sized to seal the opening and an outer face. A horizontal support rail is mounted to the housing. A guidance assembly guides the door between an open position, in which items to be sterilized or disinfected are capable of being loaded into the chamber, and a closed position, in which the door covers the opening. The guidance assembly includes a pivotable support member, pivotally connected with the door. The pivotable support member is carried by the rail during opening and closing of the door.

In accordance with another aspect of the present invention, a method of guiding a sliding door between an open position, in which access is provided to the interior of a steam cabinet through an opening defined in the cabinet, and a closed position, in which the opening is covered by the door is provided. The method includes suspending the door from a pivotable support member which is pivotally connected with the door and rolling a roller which is rotatably connected to the pivotable support member along a horizontal track mounted adjacent the opening.

One advantage of the present invention is that the door is fully guided along the entire length of its travel.

Another advantage of the present invention is that the guidance system provides axial translation for pressure load reversals within the sterilizer.

Another advantage of the present invention is that the door locks automatically, in response to pressure changes within the chamber.

Another advantage of the present invention is that the motor drive cable and pulley door actuation system eliminates the need for a door obstruction sensor, thereby simplifying the design and providing an inherently safe system.

Still further advantages of the present invention will become apparent to those of ordinary skill in the art upon reading and understanding the following detailed description of the preferred embodiment.

BRIEF DESCRIPTION OF THE DRAWINGS

The invention may take form in various components and arrangement of components and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
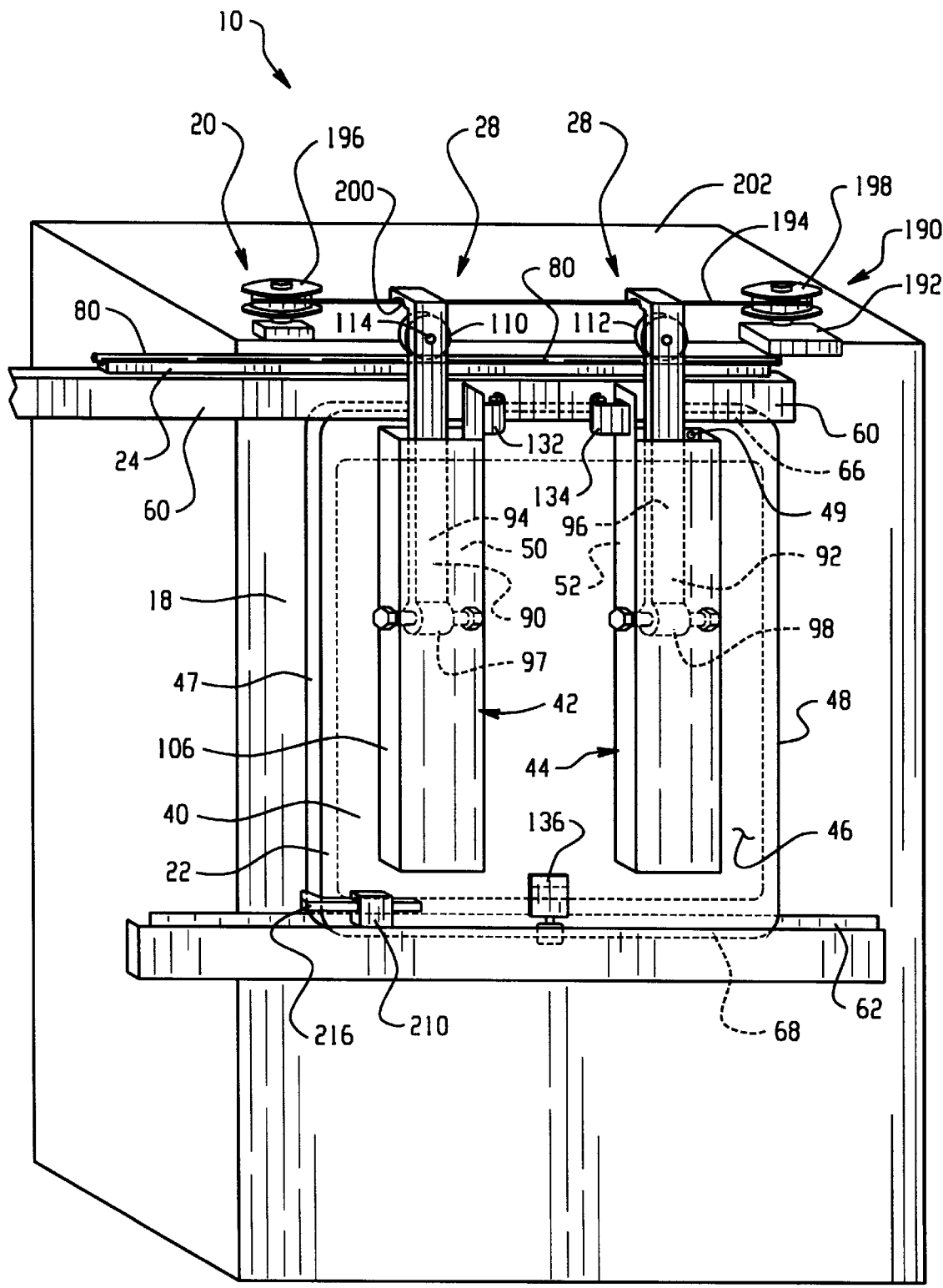
FIG. 1 is a front perspective view of a steam sterilizer with a horizontal sliding door, in accordance with the present invention.

With reference to FIGS. 1–4, a steam decontamination apparatus for sterilizing or disinfecting items includes a cabinet 10 which defines an interior chamber 12. As used herein, the term "decontamination" and similar terms encompass sterilization, disinfection, and other forms of antimicrobial treatment.

Items to be sterilized or disinfected (i.e., decontaminated) are loaded into the chamber 12 through an opening 16 in a front wall such as an end frame 18 of the cabinet 10. A horizontal sliding door assembly 20 includes a horizontal sliding door 22, a support system 24 mounted to the front wall of the cabinet for supporting the weight of the door during translation and limiting outward movement of the door, and a guidance assembly 28, carried by the door, which allows in and out movement of the door 22 in a direction perpendicular to the end frame 18 of the sterilizer.

The door 22 includes a pressure plate 40 which is sized to cover the opening 16. The pressure plate is formed from a material which is resistant to the environment within the chamber and is able to withstand the pressure changes experienced in the chamber during a decontamination cycle.

The door includes two vertically extending structural channels 42 and 44, which are mounted to a front face 46 of the pressure plate 40, adjacent left and right vertical sides 47, 48 of the plate, respectively. The channels are welded or otherwise rigidly attached to the pressure plate. The structural channels buttress the left and right vertical sides 47, 48 of the pressure plate (i.e., the trailing edge and leading edge of the door, respectively) against flexing outward or inward under the pressures experienced during sterilization, and thus preferably extend close to the full length of the pressure plate. The structural channels 42, 44 are box-shaped and define an internal cavity 50, 52, respectively. optionally, a cosmetic cover (not shown) covers the front of the door, screening the pressure plate 40 and structural channels 42, 44 from view.

The support system 24 includes upper and lower horizontally extending L-shaped restraining members 60, 62 which are mounted to the end frame of the sterilizer above and below the opening 16, respectively, and receive upper and lower horizontal sides 66, 68 of the pressure plate, respectively. A seal 70 extends around the periphery of the opening 16 in the end frame 18 of the cabinet for sealingly engaging an interior face 72 of the pressure plate when the door is in the closed position. Preferably, the seal 70 is an active seal, such as a gasket which is mounted in a groove 74 on the end frame or other exterior surface of the cabinet, best shown in FIG. 4. When the seal 70 is activated, such as by pressurizing the gasket with steam, the gasket extends outwardly and the door plate 40 is pushed outwardly toward vertically extending forward portions 76, 78 of the L-shaped restraining members 60, 62, respectively. The restraining members 60, 62 thus limit outward movement of the door during a sterilization cycle and buttress the top 66 and bottom 68 of the door against flexing. The door is thus buttressed adjacent all four sides 47, 48, 66, 68 of the pressure plate during the pressure phases of a sterilization cycle.

When pressure is applied to the plate 40 from within the sterilizer chamber 12, the door moves outward slightly, until met by the resistance provided by the forward portions 76, 78 of the restraining members. The seal 70 is configured for maintaining sealing contact with the pressure plate 40 during this outward movement. When the pressure within the chamber 12 is reduced below atmospheric pressure, the door moves inward, toward the end frame 18.

The support system 24 also includes a horizontal, cylindrical support rail 80, which is rigidly mounted to an upper horizontal surface 82 of the upper restraining member 60, by a mounting bracket 84, or other suitable mounting member, such that the rail extends above, and to the left of the opening 16, a spaced distance out from the end frame.

The guidance assembly 28 includes two pivotable supports 90, 92, which mount the door to the support rail 80. Specifically, a left pivotable support 90 is pivotally connected to the left structural channel 42 and the right pivotable support 92 is pivotally connected to the right structural channel. It is contemplated that three or more structural channels and corresponding pivotable supports may be used for large sized doors, or that only a single pivotable support be used. However, for conventional sterilizer sizes, two pivotable supports are sufficient to carry the weight of the door 22.

Each pivotable support 90, 92 includes a vertically extending rod or bar 94, 96, respectively. A lower end 97, 98 of each bar, respectively, is received within the cavity 50, 52 of the corresponding structural channel. Each lower end 97, 98 has a suitably positioned bore 100 formed therein which receives a horizontal pivot pin 102, 104 therethrough. The pivot pins are supported at either end by side portions 106, 108 of each of the structural channels 42, 44, respectively. In this way, the pivotable supports 90, 92 are pivotally connected via the lower end of each bar to the corresponding bracket.

When the pivotable supports 90, 92 are hung from the support rail 80, the door 22 is able to pivot about the pivot pins 102, 104. As the door moves in and out during pressure changes in the chamber, the pivotable supports 90, 92 independently pivot on their respective structural channels 42, 44, thereby removing stresses which would otherwise develop in a rigidly connected support. Specifically, as the pressure decreases inside the chamber and the door moves inward, the pivotable support pivots about the pivot point in the direction P (see FIG. 5). As the pressure increases inside the chamber and the door moves outward, the pivotable support pivots in the direction P'.

Figure 4:
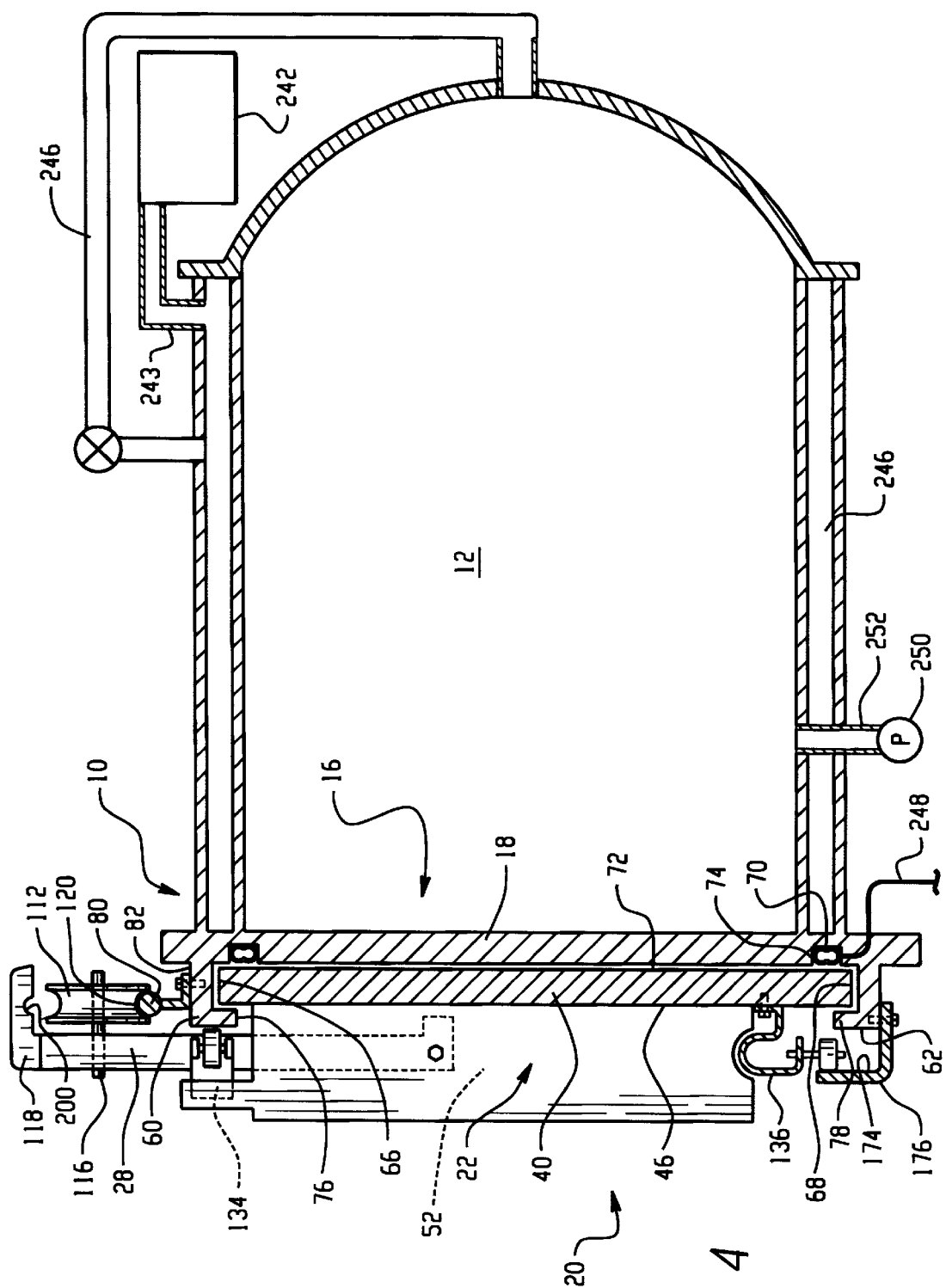
FIG. 4 is a side view of the sterilizer of FIG. 1.

For each pivotable support 90, 92, a roller 110, 112 is rotatably carried on a rearwardly extending pin 114, 116, which is mounted to the bar 94, 96 adjacent an upper end 118 of the pivotable support (see FIG. 4). The rollers 110, 112 are shaped with a circumferential groove 120 for engaging an upper surface of the cylindrical rail 80. This provides a pivot point for the door during in and out movement. The circumferential groove also keeps the roller on the rail such that the roller rolls along the rail during left and right translation of the door 22. The door 22 is thus hung by the pivotable supports from the rail 80, the weight of the door producing a downward force F on the rail 80.

Figure 5:
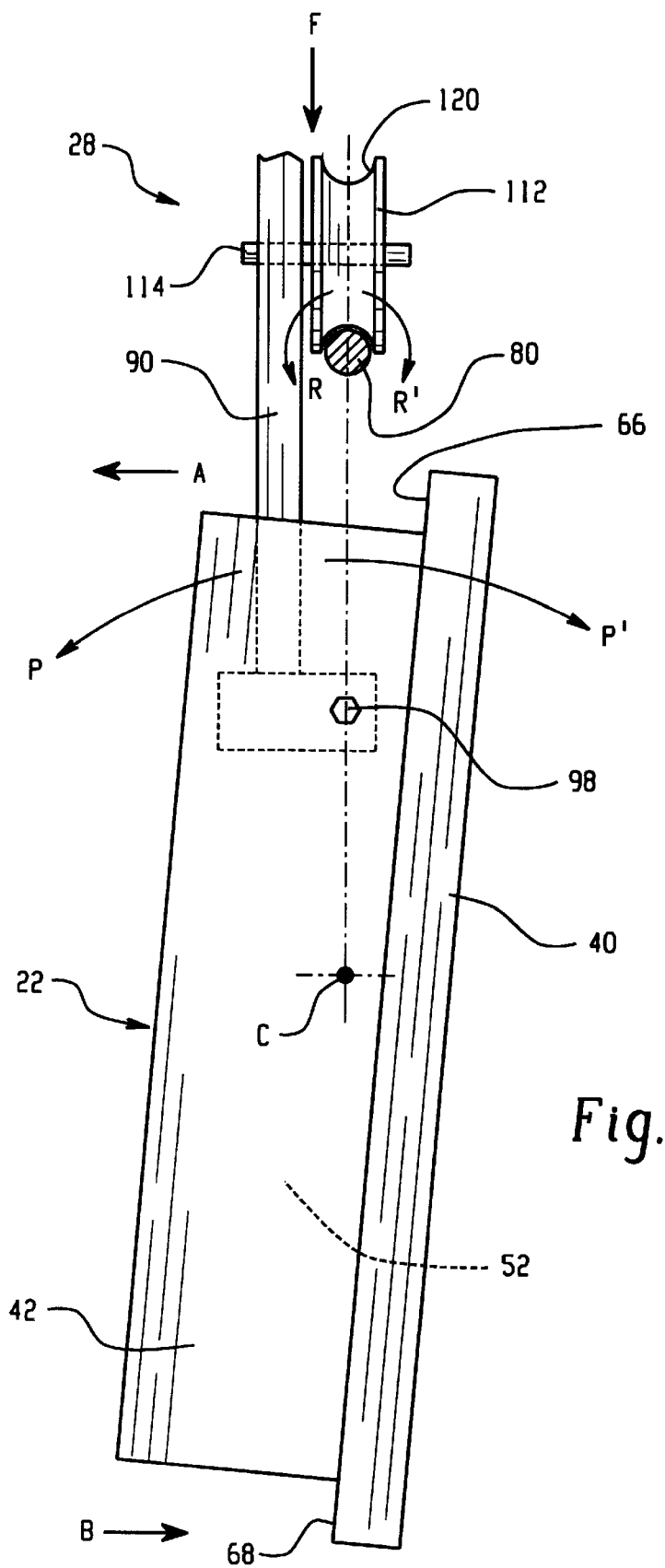
FIG. 5 is a side view of the door of FIG. 1.
Figure 6:
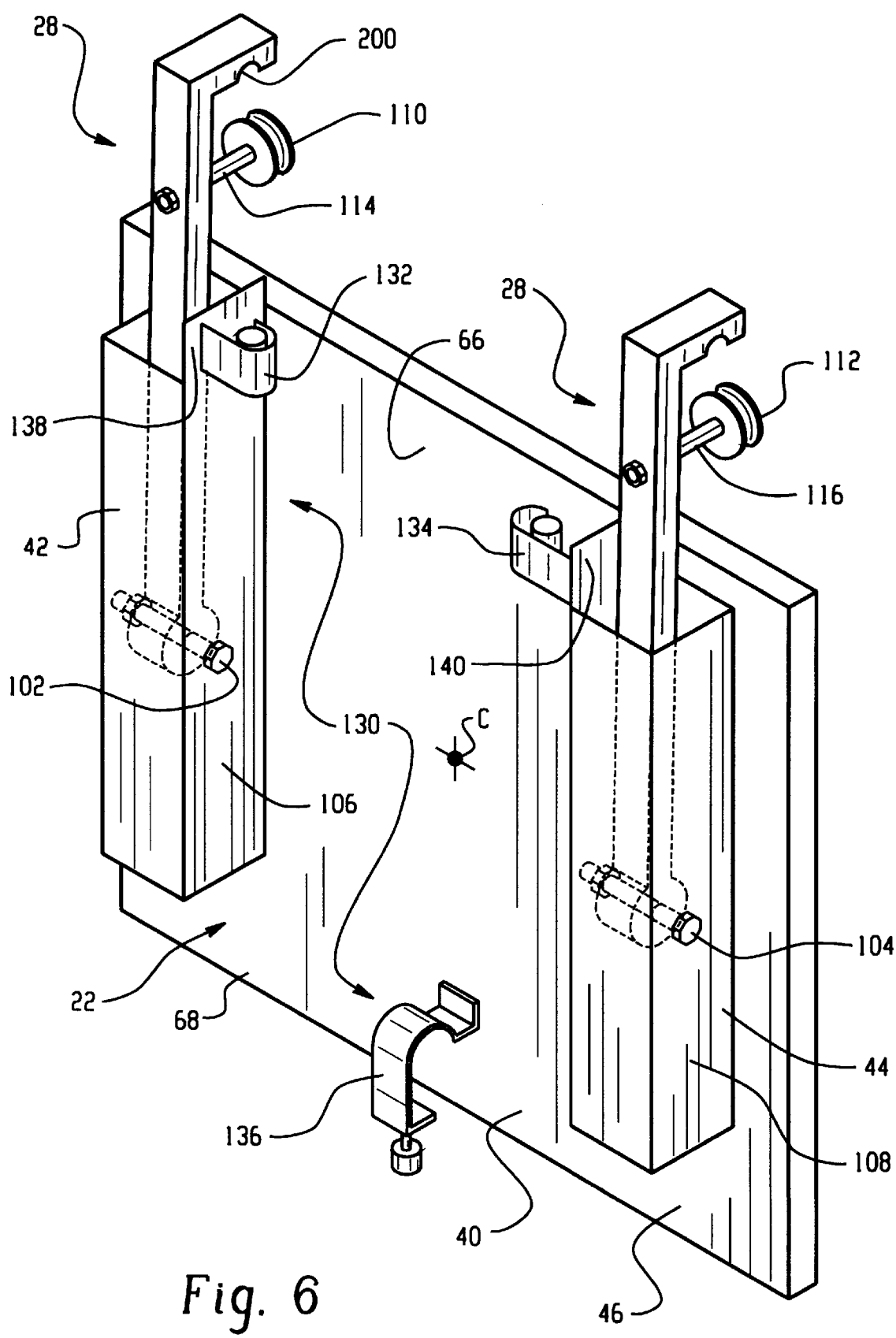
FIG. 6 is a perspective view of the door of FIG. 1.

As shown in FIGS. 1 and 5–6, the pivot points 102, 104 are located in the top half of the door 22, above the center of gravity C of the door. The center of gravity C of the door is thus such that, without restraint, the door is angled inwards (i.e., towards the chamber 12) at the top 66 of the door and outward (away from the chamber) at the bottom 68 of the door when it hangs freely from the pivotable support 90, 92. As seen in FIG. 5, when freely hanging, the center of gravity C, pivot point 98 and roller 80 are aligned vertically with one another.

A door positioning system 130, such as a system of spring-biased rollers, or other door positioners, provide the reacting forces represented by arrows A and B in FIG. 5, which maintain the door 22 in a generally vertical position. The door positioning system allows the door to move between open and closed positions without contacting the end frame 18 and seal 70 or the restraining bars 60, 62. The door positioning system also permits the door to move in and out under the influence of changing pressure within the chamber and contact the end frame 18 or restraining bars 60, 62. Preferably, the forces applied by the spring rollers are relatively small.

The system 130 of door positioners includes two upper door positioners, such as spring rollers 132, 134, and a lower door positioner, such as a spring roller 136. The upper door positioners are mounted to flanges 138, 140 which extend upwardly from the inner side portions 106, 108 of the left and right structural channels 42, 44, respectively.

Figure 7:
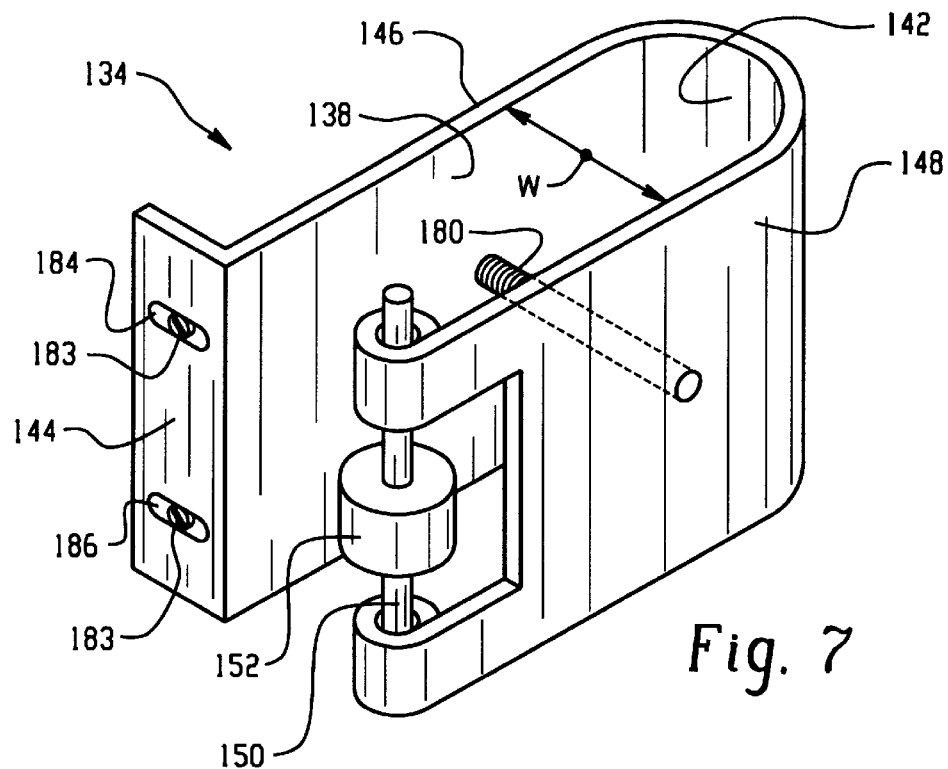
FIG. 7 is an enlarged perspective view of an upper spring roller of FIG. 1.

With reference to FIGS. 6 and 7, the upper door positioners 132, 134 each include a resiliently flexible U-shaped plate 142 or other biasing element, such as a spring. The biasing element is preferably preloaded. By preloaded, it is meant that the positioner is already under tension, so that a small additional deflection results in the generation of a significant resistive force. For convenience, only the right hand door positioner 134 is shown. It will be appreciated that the left hand door positioner 132 is a mirror image of the right hand door positioner. A flange 144 on an outer arm 146 of the U-shaped plate is mounted to the respective structural channel flange 138, 140, with screws, bolts, or other convenient attachment members. An inner arm 148 of the U-shaped plate 142 carries a vertically extending pin 150 at an outer end thereof on which a roller 152 is rotatably mounted. The roller 152 rollingly engages an upper guide surface, such as a forward outer surface 154 of forward portion 76 of the upper restraining member 60, as the door translates. The U-shaped plate 142 is resiliently flexible so that the door 22 is able to move in and out by a small amount under the changing pressure within the sterilizer. As the door 22 moves inward, under a sub-atmospheric pressure within the chamber 12, the U-shaped plates of the upper door positioners are placed under stress (i.e., the width w between the inner and outer arms 148, 146 of the plate is reduced, creating tension in the plate). The stress assists in returning the door to its original position when the pressure in the chamber is returned to atmospheric pressure and the stress is relieved. The door positioners 132, 134 function independently, such that one U-shaped plate may be placed under greater or lesser stress at any one time. While three or more upper door positioners may be used in place of two, this is not necessarily advantageous, since it is likely that only two of the rollers may make contact with the restraining member at any one time.

Figure 8:
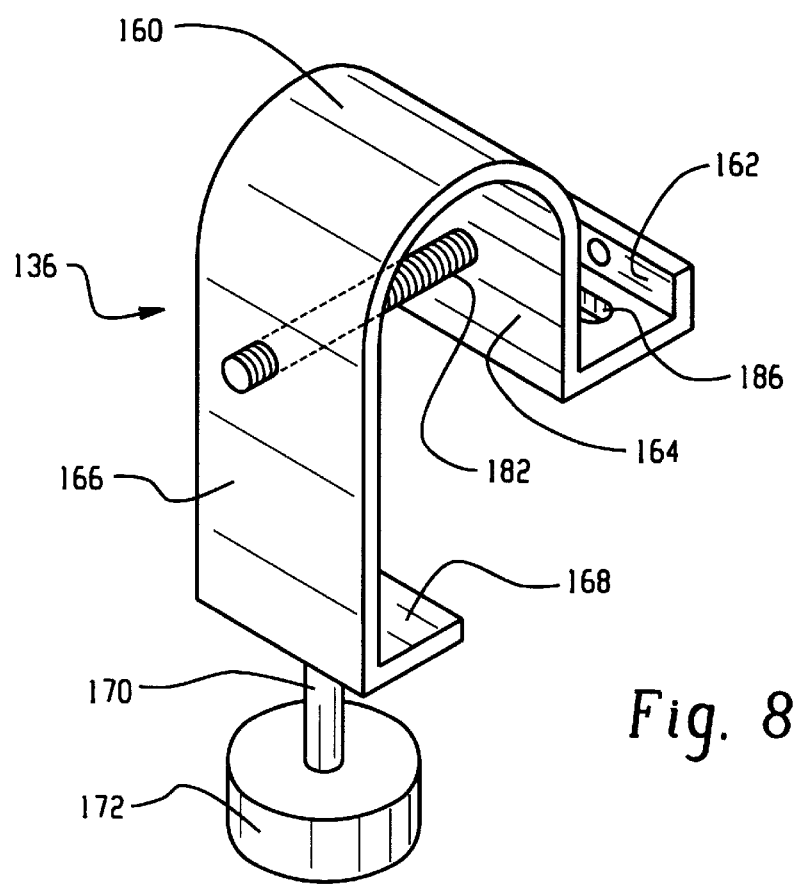
FIG. 8 is an enlarged perspective view of the lower spring roller of FIG. 1.

With reference to FIGS. 6 and 8, the lower door positioner 136 is centrally mounted to the front face 46 of the pressure plate 40 adjacent the lower end 68 of the door. The lower door positioner includes a U-shaped plate 160, which functions similarly to the U-shaped plate of the upper door positioners. In this case, however, the U-shaped plate is vertically, rather than horizontally aligned, with a mounting flange 162 extending from an inner arm 164 of the U-shaped plate. An outer arm 166 of the U-shaped plate has an inwardly extending flange 168 at its lower end. A vertically extending pin 170 hangs from the flange 168 and carries a roller 172 thereon. During translation of the door, the roller 172 rollingly engages a lower guide surface, such as a vertical inner surface 174 of an L-shaped roller guide 176 which is mounted forwardly of the lower restraining member 62 (see FIG. 4). As the pressure increases within the sterilizer above atmospheric, the door moves outwardly until it engages the restraining members 60, 62. The U-shaped plate 160 of the lower door positioner is placed under stress during this movement, which helps to return the door to its original position when the pressure excess is removed.

The upper door positioners 132, 134 thus bias the top of the door outward in the direction of arrow A, while the lower door positioner 136 biases the door inward in the direction of arrow B, thereby positioning the door vertically, while also allowing in and out movement of the door under the effects of pressure changes within the sterilizer. It should be understood that the term bias is used herein to indicate that the door is being moved to a vertical position, rather than to a skewed position.

Preferably, the door positioners 132, 134, 136 are positioned such that the rollers make contact with the guide surfaces 154, 174, respectively. It is preferable to have only a single door positioner 136 at the bottom center of the door, rather than an additional fourth door positioner. This ensures that each of the door positioners 132, 134, 136 is making contact with its respective contact surface 154, 174 at all times. Spacing members 180, 182 connect the inner and outer arms of the U-shaped plate to provide the preload. Adjustment of the preload (initial tension) on the door positioners is achieved through adjustment of screws 183 which are received through suitably positioned elongated mounting slots 184, 186 in the mounting flange 182. The screws 183 are adjusted in the slots, as necessary, after the door 22 has been hung in position, to align the door vertically. The adjustment changes the position of the rollers and the force they apply.

While the system of door positioners has been described with reference to door positioners 132, 134 at the top of the door which restrain the top of the door from moving inward and a door positioner 136 at the bottom of the door which restrains the bottom of door from moving outward, it is also contemplated that the center of gravity C of the door could be positioned such that, without restraint, the door tends to lean inward at the bottom and outward at the top, i.e., opposite to that shown in FIG. 5. In such an embodiment, one or two upper springs similar to the lower springs 136, could be used to bias the top of the door inward, and one or two lower springs, similar to the upper springs 132, 134 could be used to bias the bottom of the door outward.

Figure 9:
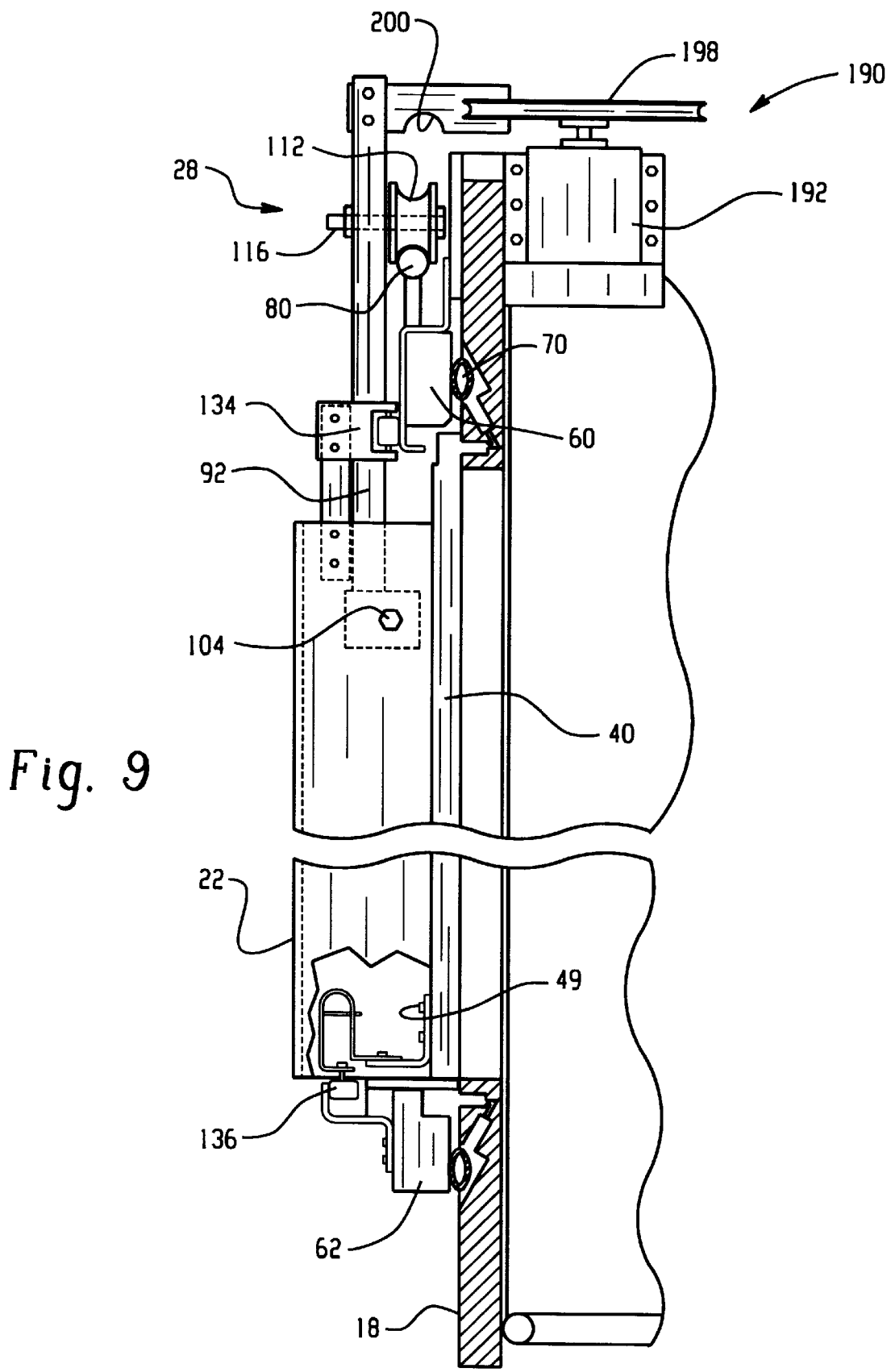
FIG. 9 is a side view of the forward end of the sterilize of FIG. 1.

With reference to FIGS. 1 and 9, a drive system 190 moves the door 22 between open and closed positions. The drive system includes a motor 192, which drives a cable 194 between two pulleys 196, 198. The cable 194 is connected to the upper end 118 of each of the pivotable supports 90, 92. The two pulleys 196, 198 are mounted to brackets attached to the end frame adjacent an upper wall 202 of the cabinet (or to the top of the motor 192, in the case of pulley 198) to support the cable 194 at either end of the cabinet opening 16. When the motor 192 is actuated, the cable 194 pulls the pivotable supports 90, 92, and the support rollers 110, 112 roll along the rail 80 carrying the door 22 between the open and closed positions.

The cable tension is preferably such that slippage of the cable or stalling of the motor occurs at a preselected driving force, preferably around 10 to 15 kilograms force, more preferably, no greater than 13.6 kilograms force. If an obstruction is positioned in the path of the door, the motor 192 will stall and/or the cable will slip when the predetermined driving force is achieved. This prevents injury or damage from occurring to the obstruction, and avoids the need for a complex system of sensors to detect the absence of obstructions.

Figure 10:
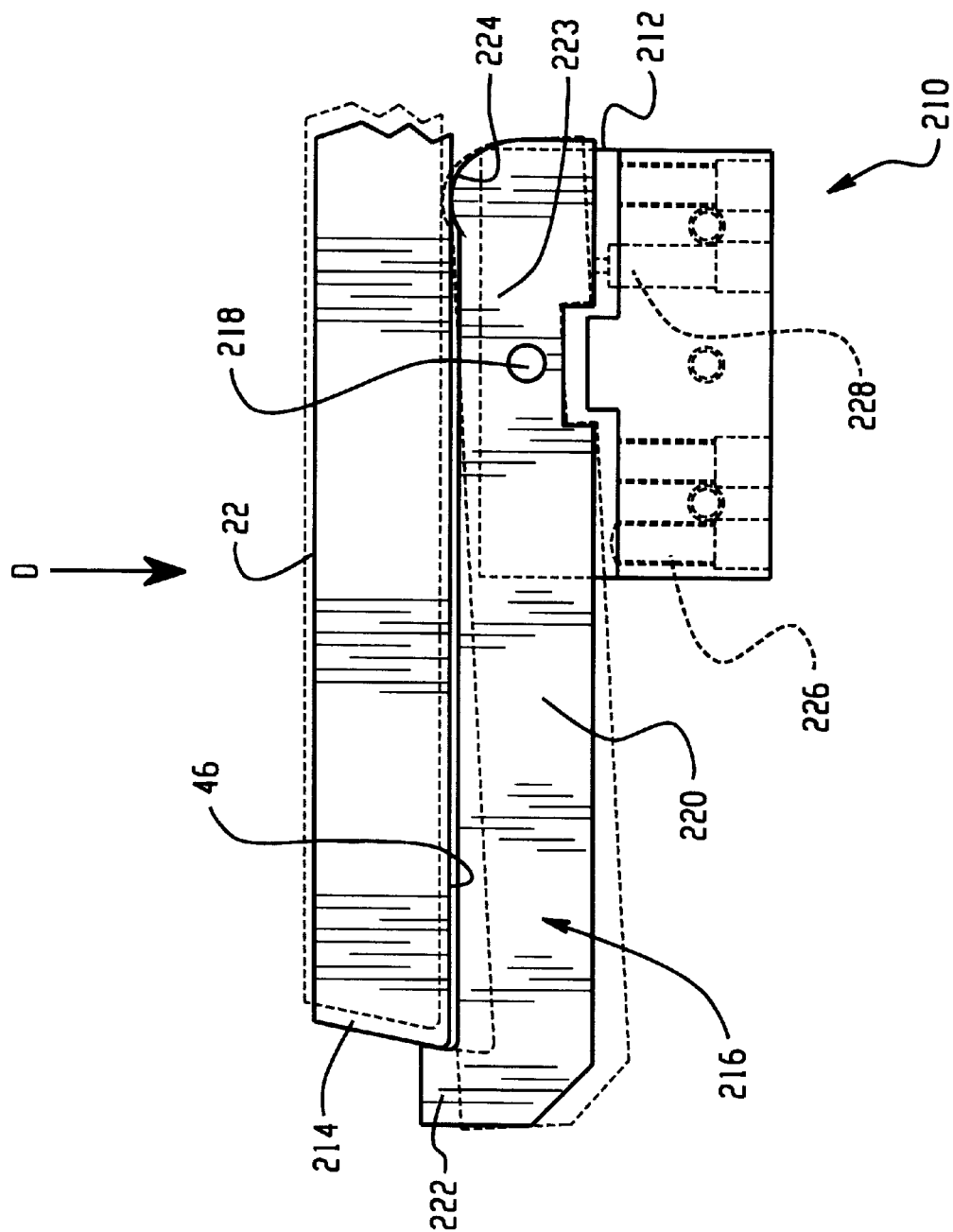
FIG. 10 is an enlarged view of the locking mechanism of FIG. 1 through line A—A.

With reference to FIGS. 1 and 10, a door locking mechanism 210 prevents the door from opening during the pressure phase of the sterilizing cycle (i.e., when the pressure within the chamber 12 is above-atmospheric). In a preferred embodiment, the door locking mechanism is actuated by the pressure within the chamber. As shown in FIG. 10, the locking mechanism includes a bracket or support 212, which is mounted to the top of the lower restraining bar 62, adjacent the trailing edge 47 of the door, when the door is in the closed position. A lever 216 is pivotally connected to the support 212 at a pivot point 218. A first portion 220 of the lever 216 extends in one direction, from the pivot point, towards the trailing vertical edge 47, and has a hook 222 at a distal end thereof for engaging the trailing edge of the door when the mechanism is in a locked position. A second portion 223 of the lever extends from the pivot point, in the opposite direction and has a projection 224 at a distal end thereof, which faces the outer surface 46 of the pressure plate. During opening and closing, the door (shown in phantom) translates freely past the hook 222 of the lever (also shown in phantom), without hindrance. A set screw 226, mounted on the support, adjacent the first portion 220 of the lever, limits outward movement of the first portion of the lever to avoid hindrance by the protrusion. When pressure is applied to the door 22 from the direction of arrow D (i.e., when the pressure within the chamber 12 is above atmospheric), the front face 46 of the door applies pressure to the protrusion 224 on the lever. Pressure on the protrusion pivots the lever about the pivot point 218, causing the hook 222 of the lever to move to the position shown in full lines, where it engages the trailing edge 47 of the door plate 40. This prevents the door from being opened during the pressure portion of the cycle.

When the outward pressure on the door is relieved, the lever 216 is pivoted back to its original position and the door is free to move once more. A spring or piston 228, mounted on the support adjacent the second portion 223 of the lever, assists in returning the lever to its original position once the outward pressure is removed.

While the door locking mechanism 210 provides a simple mechanical lock for the door, other door locking mechanisms, in addition to, or in place of mechanism 210 are also contemplated. For example, an electronically or pneumatically actuated mechanical stop may be employed in place of, or in addition to the lock mechanism described.

Figure 2:
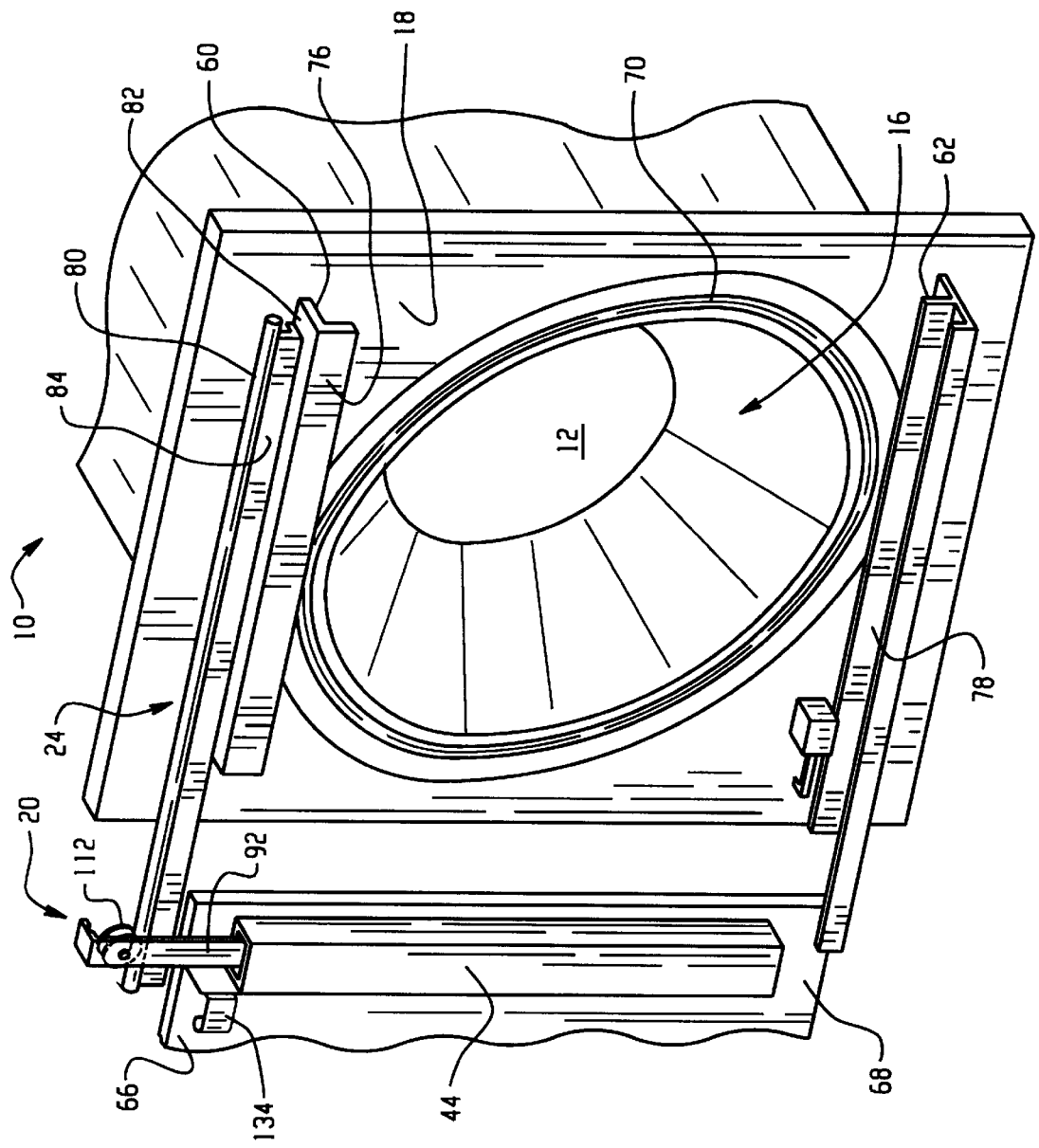
FIG. 2 is a perspective view of the sterilizer of FIG. 1, with the door in an open position.
Figure 3:
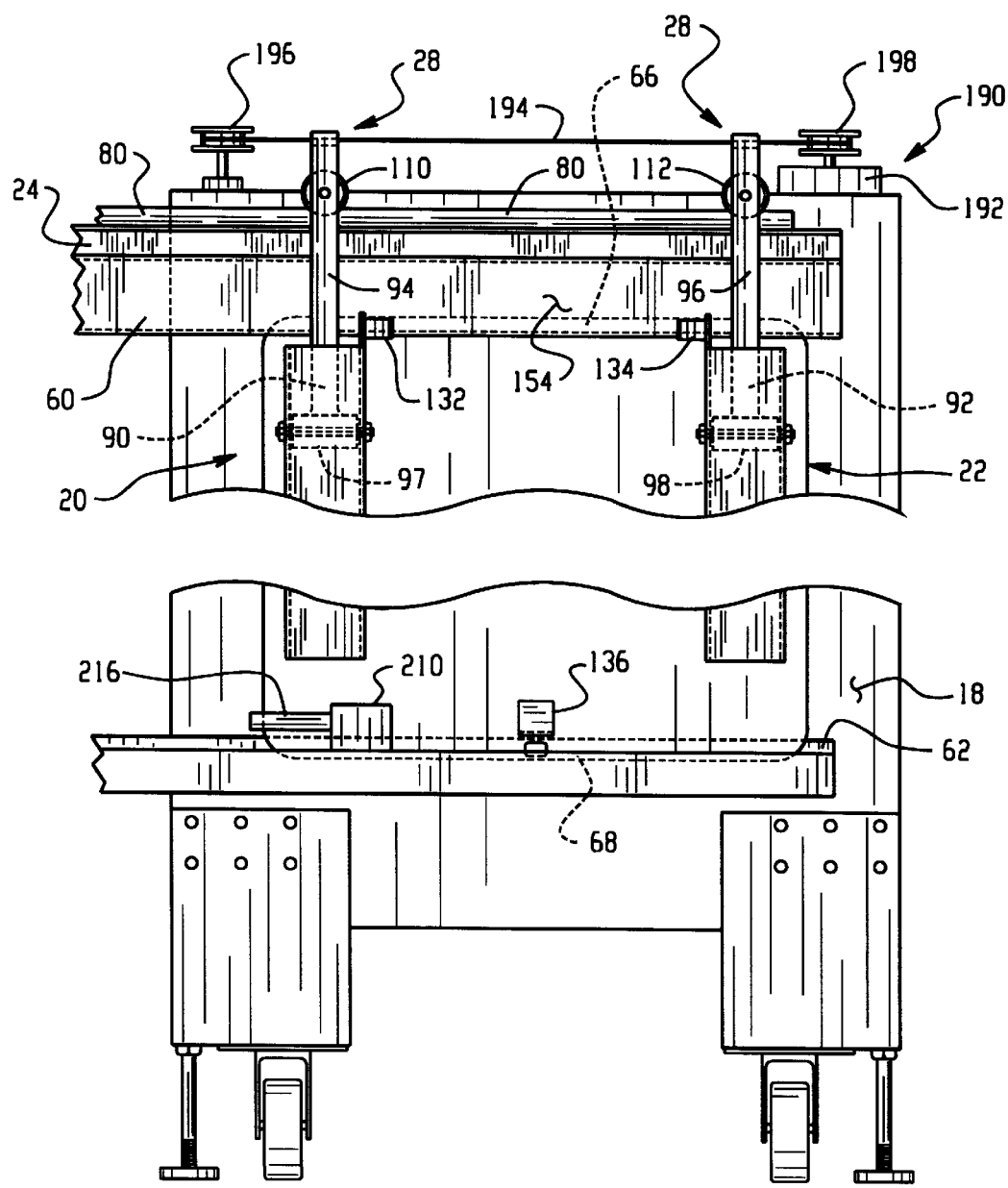
FIG. 3 is a front view of the sterilizer of FIG. 1.

The sterilizing or disinfecting apparatus is operated by first loading items to be decontaminated through the opening 16 into the chamber 12 while the door is in the open position illustrated in FIG. 2. The door is then moved into the closed position by operating the motor-driven cable and pulley door actuation system 190. During opening and closing the door, the support rollers 110, 112 run along the rail 80 and carry the weight of the door. The door is guided at the bottom by the lower door positioner 136 and by the upper door positioners 132, 134 at the top. The door 22 thus slides across the opening, centered between the end frame 18 and the restraining bars, thereby avoiding scraping the front of the end frame or damaging the seal. The positioning of the slots of the slotted door positioners are adjusted, as needed during the lifetime of the sterilizer, to maintain this small gap at both top and bottom of the door.

With reference to FIG. 4, a sterilization or other antimicrobial decontamination cycle is then carried out. Specifically, the cycle may include one or more pressure phases, in which steam is introduced to the chamber through an inlet pipe 240 from a boiler 242, or other source of steam. The steam from the boiler may also be used to heat an insulating jacket 246, via the same or a separate inlet pipe 243, and to pressurize the gasket 70, via a gasket inlet line 248. The decontamination cycle may also include one or more vacuum phases, in which a vacuum is applied to the chamber 12, such as by operating a vacuum pump 250, connected with the chamber by a vacuum line 252.

The multi-pivot design provided by the door positioners and pivotable supports allows the door to move in and out between the restraining members and end frame 18 during the pressure and vacuum phases of the sterilization cycle. When the pressure is increased within the chamber, the door lock 210 operates. The pressure plate 40 moves slightly outwards and the pivotable supports 90, 92 pivot around their pivot points 102, 104 to prevent any stresses on the pivotable supports. Similarly, when the pressure inside the chamber is reduced to below atmospheric pressure, the door plate 40 is drawn inward towards the end frame 18 of the sterilizer, and the pivotable supports once again pivot around their respective pivot points. The pivotable support rollers 110, 112 rotate slightly on the rail during the in and out movement of the door in the direction of arrows R and R' (see FIG. 5). The U-shaped plates 142, 160 flex to allow the door 22 to move in and out. The lever 216 of the lock mechanism is pivoted into engagement with the trailing edge 47 of the door during the pressure portion of the cycle.

At the end of the sterilization or disinfection cycle, the drive motor 192 is actuated to drive the cable 194 in an opposite direction to the closing direction, to open the door 22 once more. The decontaminated items are then removed from the chamber 12.

In the event of a power failure or motor 192 failure, the sterilizer door 22 can be opened or closed by hand, simply by pushing the door. There is no need for a crank or other mechanical emergency opening system, as with conventional door systems.

While the door 22 is shown in FIGS. 1 and 2 as closing from left to right, it will be appreciated that the door may be converted to a right-to-left closing door by adjusting the position of the support rail 80 so that it extends to the right of the opening 16, rather than to the left. The locking mechanism 210 is replaced with an analogous (essentially a mirror image) locking mechanism adjacent the right side of the door.

While the door has been described with respect to an overhead pivotable support system, it is also contemplated that the door may be supported from below, by similar pivotable supports to those described above, but which support the weight of the door from below. In this embodiment, the pivotable support rollers preferably run on a rail positioned below the opening. A similar door positioning system to that described above is preferably used to maintain the door in vertical alignment.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A sterilization or disinfection apparatus comprising:
   a housing which defines an interior chamber and an opening;
   a door having an interior face sized to seal the opening and an outer face;
   an active seal between the door and the housing surrounding the opening to the chamber which seal is selectively pressurized to seal against the door and push the door outward, away from the housing;
   a horizontal support rail mounted to the housing;
   a guidance assembly for guiding the door between an open position, in which items to be sterilized or disinfected are capable of being loaded into the chamber, and a closed position, in which the door covers the opening, the guidance assembly including:
      a pivotable support member, pivotally connected with the door, which pivots as the door moves outward during pressurization of the active seal, the pivotable support member being carried by the rail during opening and closing of the door.

2. A sterilization or disinfection apparatus comprising:
a housing which defines an interior chamber and an access opening;
a door having an interior face sized to cover the access opening;
a horizontal support rail mounted to the housing; and
guidance assembly for guiding the door between an open position, in which items to be sterilized or disinfected can be passed through the access opening, and a closed position, in which the door covers the access opening, the guidance assembly including:
a pivotable support member, pivotally connected with the door, the pivotable support member being carried by the rail during opening and closing of the door, the pivotable support member pivoting about the door in response to pressure changes within the chamber.

3. The apparatus of claim 2, wherein the support member includes a roller which rollingly engages the support rail during opening and closing of the door.

4. The apparatus of claim 2, wherein the pivotable support member is pivotally connected with an outer face of the door.

5. The apparatus of claim 2, comprising two pivotable support members.

6. The apparatus of claim 2, further including:
a seal between the door and the housing surrounding the opening to the chamber which selectively seals against the door, the guidance assembly maintaining a space between the door and the housing when the door is moving between the open and closed positions.

7. A sterilization or disinfection apparatus comprising:
a housing which has an interior chamber and an opening;
a door with an interior face sized to cover the opening;
a horizontal support rail mounted to the housing;
a guidance means for guiding the door between an open position and a closed position, in which the door covers the opening, the guidance assembly including:
a pivotable support member including a bar which is pivotally connected with the door adjacent a lower end and a roller which rollingly engages the support rail during opening and closing of the door, the roller being connected with the bar and being spaced upwardly from the lower end.

8. A sterilization or disinfection apparatus comprising:
a housing which defines an interior chamber and an opening;
a door having an interior face sized to seal the opening;
a support rail mounted to the housing;
a guidance assembly which guides the door between an open position, in which items to be sterilized or disinfected are capable of being loaded into the interior chamber, and a closed position, in which the door covers the opening, the guidance assembly including:
a support member, connected with the door, the support member being carried by the rail during opening and closing of the door; and
a door positioning system which biases a top of the door in a first direction and biases a bottom of the door in a second direction generally opposite to the first direction to maintain the door in a generally vertical orientation.

9. The apparatus of claim 8, wherein the door positioning system includes one or more upper positioning members mounted to the door adjacent an upper side of the door and one or more lower positioning members mounted to the door adjacent a lower side of the door.

10. The apparatus of claim 9, wherein the upper positioning members engage an upper guide surface, mounted to the housing above the opening and the lower positioning members engage a lower guide surface, mounted to the housing below the opening.

11. The apparatus of claim 10, wherein the positioning members comprise spring biased rollers which rollingly engage the guide surface during opening and closing of the door.

12. The apparatus of claim 11, wherein the spring biased rollers each include:
a rolling member; and
a resiliently flexible support which mounts the rolling member to the door and which allows the door to move in a direction perpendicular to the opening, in response to pressure changes within the chamber.

13. The apparatus of claim 8, further including restraining members, mounted to the housing, which limit outward movement of the door.

14. A sterilization or disinfection apparatus comprising:
a housing surrounding an interior chamber and defining a port;
a door including:
a pressure plate which defines an interior face sized to cover the access port, and
a vertically extending channel, attached to the pressure plate;
a horizontal support rail mounted to the housing; and
a pivotable support member pivotally connected with the vertically extending channel, the pivotable support member being supported by the rail for movement therealong during opening and closing of the door.

15. A sterilization or disinfection apparatus comprising:
a housing which defines an interior chamber and an opening;
a door having an interior face sized to seal the opening;
a horizontal support rail mounted to the housing;
a support member, connected with the door, the support member being carried by the rail during opening and closing of the door; and
a locking mechanism which locks the door against opening when the door moves outward in response to an above-atmospheric pressure within the chamber.

16. The apparatus of claim 15, wherein the locking mechanism includes a pivotable lever which includes:
a projection at a first end of the lever; and
a hook at a second end of the lever, the door applying pressure on the projection as the door moves outward, pivoting the hook into locking engagement with the door.

17. A sterilization or disinfection apparatus comprising:
a housing which defines an interior chamber and an opening;
a door having an interior face sized to seal the opening;
a horizontal support rail mounted to the housing;
a guidance assembly for guiding the door between an open position, in which items to be sterilized or disinfected are capable of being loaded into the chamber, and a closed position, in which the door covers the opening, the guidance assembly including:
a pivotable support member, connected with the door, the pivotable support member being carried by the rail during opening and closing of the door; and
a drive system which drives the door between the open and closed positions, the drive system including:

a motor; and a cable, the cable being driven by the motor and connected with the pivotable support member.

18. The apparatus of claim 17, wherein the motor stalls or the cable slips if the door encounters a resistance to movement which applies a force to the door which is above a predetermined maximum force.

19. A method of guiding a sliding door between an open position, in which access is provided to the interior of a steam cabinet through an opening defined in the cabinet, and a closed position, in which the opening is covered by the door, the method comprising the steps of:

suspending the door from a pivotable support member which is pivotally connected with the door; [and]

rolling a roller which is rotatably connected to the pivotable support member along a track mounted adjacent the opening; and changing the pressure within the cabinet, the roller pivoting on the track as the door moves perpendicularly to the opening in response to the pressure change.

20. The method of claim 19, further including:

biasing at least one of a top and a bottom of the door to maintain the door in a generally vertical orientation.

21. The method of claim 19, wherein the track has a circular cross,section and the roller has a matching circumferential groove shaped to engage the circular cross section.

22. A method of sterilizing or disinfecting comprising:

loading items into a steam chamber through an opening;

rolling a door suspended from a guide track by a support member to cover the opening;

pressurizing an active seal surrounding the opening into contact with an inner surface of the door and moving the door outward, the door pivoting about the support member during outward movement;

filling the chamber with steam under pressure;

removing the steam from the chamber and depressurizing the chamber;

depressurizing the active seal, the door pivoting about the support member and moving inward as at least one of the active seal and the chamber are depressurized;

rolling the door along the guide track to uncover the opening; and removing the items from the chamber through the opening.

* * * * *